US006941169B2

(12) United States Patent
Pappu (10) Patent No.: US 6,941,169 B2
(45) Date of Patent: Sep. 6, 2005

(54) CARDIAC STIMULATING APPARATUS HAVING A BLOOD CLOT FILTER AND ATRIAL PACER

(75) Inventor: Ramesh Pappu, Cherry Hill, NJ (US)

(73) Assignee: Albert Einstein Healthcare Network, Philadelphia, PA (US)

( * ) Notice: Subject to any disclaimer, the term of this patent is extended or adjusted under 35 U.S.C. 154(b) by 248 days.

(21) Appl. No.: 10/163,021

(22) Filed: Jun. 4, 2002

(65) Prior Publication Data

US 2002/0183823 A1 Dec. 5, 2002

Related U.S. Application Data

(60) Provisional application No. 60/295,683, filed on Jun. 4, 2001.

(51) Int. Cl.[7] .............................. A61N 1/36; A61N 1/05
(52) U.S. Cl. .......................................... 607/9; 607/122
(58) Field of Search ................................ 607/5, 9, 119, 607/122–128; 606/200

(56) References Cited

U.S. PATENT DOCUMENTS

| 178,283 A | 6/1876 | French |
| 1,967,318 A | 7/1934 | Monahan |
| 3,844,302 A | 10/1974 | Klein |

(Continued)

FOREIGN PATENT DOCUMENTS

| WO | WO 93/13712 | 7/1993 |
| WO | WO 97/28749 | 8/1997 |
| WO | WO 98/02100 | 1/1998 |

(Continued)

OTHER PUBLICATIONS

S. Mueller–Hulsbeck, et al., "Vacuum Pump Controlled Aspiration Thrombectomy: In Vitro Comparison With a Thrombus Fragmentation Procedure" Fortschr. Rontgenstr., vol. 168 (1998), No. 2 pp 191–194 (English translation).

Brossman, et al., "Percutaneous Balloon–assisted Thrombectomy: Preliminary In Vivo Results with a Expandable Vascular Sheath System[1]" Radiology 1998; vol. 206 (No. 2); 439–445.

(Continued)

*Primary Examiner*—Jeffrey R. Jastrzab
(74) *Attorney, Agent, or Firm*—John S. Child, Jr.; Niels Haun (57) ABSTRACT

An apparatus is provided for reducing the formation and migration of blood clots from an atrial appendage, such as the left atrial appendage, to the blood vessel system of a patient. The apparatus comprises an atrial pacer to treat non-rheumatic atrial fibrillation (NRAF) of an atrial appendage so that the formation blood clots within the atrial appendage is decreased or eliminated. In addition, the apparatus includes a blood clot filter supported by the atrial pacer proximate the atrial appendage and the atrium to reduce the migration of blood clots from the atrial appendage into the blood vessel system of a patient.

87 Claims, 4 Drawing Sheets

U.S. PATENT DOCUMENTS

| | | |
|---|---|---|
| 3,874,388 A | 4/1975 | King et al. |
| 3,946,731 A | 3/1976 | Lichtenstein |
| 4,007,743 A | 2/1977 | Blake |
| 4,166,470 A | 9/1979 | Neumann |
| 4,341,218 A | 7/1982 | U |
| 4,585,000 A | 4/1986 | Hershenson |
| 4,603,693 A | 8/1986 | Conta et al. |
| 4,665,906 A | 5/1987 | Jervis |
| 4,710,192 A | 12/1987 | Liotta et al. |
| 4,817,600 A | 4/1989 | Herms et al. |
| 4,832,055 A | 5/1989 | Palestrant |
| 4,917,089 A | 4/1990 | Sideris |
| 4,921,484 A | 5/1990 | Hillstead |
| 4,957,501 A | 9/1990 | Lahille et al. |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,078,736 A | 1/1992 | Behl |
| 5,108,420 A | 4/1992 | Marks |
| 5,171,259 A | 12/1992 | Inoue |
| 5,176,692 A | 1/1993 | Wilk et al. |
| 5,192,301 A | 3/1993 | Kamiya et al. |
| 5,234,403 A | 8/1993 | Yoda et al. |
| 5,256,146 A | 10/1993 | Ensminger et al. |
| 5,258,042 A | 11/1993 | Mehta |
| 5,279,546 A | 1/1994 | Mische et al. |
| 5,284,488 A | 2/1994 | Sideris |
| 5,306,234 A | 4/1994 | Johnson |
| 5,314,451 A | 5/1994 | Mulier |
| 5,329,942 A | 7/1994 | Gunther et al. |
| 5,334,217 A | 8/1994 | Das |
| 5,350,399 A | 9/1994 | Erlebacher et al. |
| 5,353,784 A | 10/1994 | Nady-Mohamed |
| 5,368,034 A | 11/1994 | Isner |
| 5,370,657 A | 12/1994 | Irie |
| 5,375,612 A | 12/1994 | Cottenceau et al. |
| 5,380,299 A | 1/1995 | Fearnot et al. |
| 5,417,699 A | 5/1995 | Klein et al. |
| 5,421,832 A | 6/1995 | Lefebvre |
| 5,425,744 A | 6/1995 | Fagan et al. |
| 5,433,727 A | 7/1995 | Sideris |
| 5,443,454 A | 8/1995 | Tanabe et al. |
| 5,451,235 A | 9/1995 | Lock et al. |
| 5,458,574 A | 10/1995 | Machold et al. |
| 5,464,408 A | 11/1995 | Duc |
| 5,469,867 A | 11/1995 | Schmitt |
| 5,490,856 A | 2/1996 | Person et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,531,779 A * | 7/1996 | Dahl et al. .................. 600/381 |
| 5,536,412 A | 7/1996 | Ash |
| 5,562,698 A | 10/1996 | Parker |
| 5,591,196 A | 1/1997 | Marin et al. |
| 5,601,595 A | 2/1997 | Smith |
| 5,607,579 A | 3/1997 | Latham, Jr. et al. |
| 5,614,204 A | 3/1997 | Cochrum |
| 5,626,605 A | 5/1997 | Irie et al. |
| 5,634,936 A | 6/1997 | Linden et al. |
| 5,634,942 A | 6/1997 | Chevillon et al. |
| 5,637,097 A | 6/1997 | Yoon |
| 5,643,292 A | 7/1997 | Hart |
| 5,649,953 A | 7/1997 | Lefebvre |
| 5,662,671 A | 9/1997 | Barbut et al. |
| 5,669,933 A | 9/1997 | Simon et al. |
| 5,681,347 A | 10/1997 | Cathcart et al. |
| 5,690,671 A | 11/1997 | McGurk et al. |
| 5,693,067 A | 12/1997 | Purdy |
| 5,695,525 A | 12/1997 | Mulhauser et al. |
| 5,702,421 A | 12/1997 | Schneidt |
| 5,709,224 A | 1/1998 | Behl et al. |
| 5,709,707 A | 1/1998 | Lock et al. |
| 5,713,849 A | 2/1998 | Bosma et al. |
| 5,725,552 A | 3/1998 | Kotula et al. |
| 5,725,568 A | 3/1998 | Hastings |
| 5,733,294 A | 3/1998 | Forber et al. |
| 5,735,290 A | 4/1998 | Sterman et al. |
| 5,746,767 A | 5/1998 | Smith |
| 5,749,883 A | 5/1998 | Halpern |
| 5,749,894 A | 5/1998 | Engelson |
| 5,766,219 A | 6/1998 | Horton |
| 5,769,816 A | 6/1998 | Barbut et al. |
| 5,776,097 A | 7/1998 | Massoud |
| 5,782,860 A | 7/1998 | Epstein et al. |
| 5,792,207 A | 8/1998 | Dietrich |
| 5,800,454 A | 9/1998 | Jacobsen et al. |
| 5,800,457 A | 9/1998 | Gelbfish |
| 5,810,874 A | 9/1998 | Lefebvre |
| 5,823,198 A | 10/1998 | Jones et al. |
| 5,827,229 A | 10/1998 | Auth et al. |
| 5,830,228 A | 11/1998 | Knapp et al. |
| 5,836,913 A | 11/1998 | Orth et al. |
| 5,836,968 A | 11/1998 | Simon et al. |
| 5,846,260 A | 12/1998 | Maahs |
| 5,846,261 A | 12/1998 | Kotula et al. |
| 5,849,005 A | 12/1998 | Garrison et al. |
| 5,851,232 A | 12/1998 | Lois |
| 5,855,597 A | 1/1999 | Jayaraman |
| 5,858,238 A | 1/1999 | McRea et al. |
| 5,865,791 A | 2/1999 | Whayne et al. |
| 5,865,802 A | 2/1999 | Yoon et al. |
| 5,868,708 A | 2/1999 | Hart et al. |
| 5,873,894 A | 2/1999 | Vandegriff |
| 5,876,367 A | 3/1999 | Kaganov et al. |
| 5,882,340 A | 3/1999 | Yoon |
| 5,885,258 A | 3/1999 | Sachdeva et al. |
| 5,891,178 A | 4/1999 | Mann |
| 5,895,399 A | 4/1999 | Barbut et al. |
| 5,904,680 A | 5/1999 | Kordis |
| 5,904,703 A | 5/1999 | Gilson |
| 5,906,207 A | 5/1999 | Shen |
| 5,910,154 A | 6/1999 | Tsugita et al. |
| 5,911,734 A | 6/1999 | Tsugita et al. |
| 5,916,236 A | 6/1999 | Muijs Van de Moer et al. |
| 5,925,063 A | 7/1999 | Khosravi |
| 5,928,192 A | 7/1999 | Maahs |
| 5,928,260 A | 7/1999 | Chin et al. |
| 5,935,147 A | 8/1999 | Kensey et al. |
| 5,935,148 A | 8/1999 | Villar et al. |
| 5,938,645 A | 8/1999 | Gordon |
| 5,941,249 A | 8/1999 | Maynard |
| 5,947,997 A | 9/1999 | Pavcnik et al. |
| 5,951,589 A | 9/1999 | Epstein et al. |
| 5,954,694 A | 9/1999 | Sunseri |
| 5,957,940 A | 9/1999 | Tanner et al. |
| 5,976,174 A | 11/1999 | Ruiz |
| 5,980,555 A | 11/1999 | Barbut et al. |
| 5,989,281 A | 11/1999 | Barbut et al. |
| 5,993,469 A | 11/1999 | McKenzie et al. |
| 5,997,557 A | 12/1999 | Barbut et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,010,531 A | 1/2000 | Donlon et al. |
| 6,024,754 A | 2/2000 | Engelson |
| 6,024,755 A | 2/2000 | Addis |

| | | |
|---|---|---|
| 6,024,756 A | 2/2000 | Huebsch et al. |
| 6,027,520 A | 2/2000 | Tsugita et al. |
| 6,033,420 A | 3/2000 | Hahnen |
| 6,036,720 A | 3/2000 | Abrams et al. |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,059,745 A | 5/2000 | Gelbfish |
| 6,063,070 A | 5/2000 | Eder |
| 6,068,621 A | 5/2000 | Balceta et al. |
| 6,074,357 A | 6/2000 | Kaganov et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,120,496 A | 9/2000 | Whayne |
| 6,132,438 A | 10/2000 | Fleischman et al. |
| 6,136,016 A | 10/2000 | Barbut et al. |
| 6,139,527 A | 10/2000 | Laufer et al. |
| 6,146,396 A | 11/2000 | Konya et al. |
| 6,152,144 A | 11/2000 | Lesh et al. |
| 6,161,543 A | 12/2000 | Cox et al. |
| 6,178,351 B1 | 1/2001 | Mower |
| 6,235,044 B1 * | 5/2001 | Root et al. .................. 606/200 |
| 6,551,303 B1 | 4/2003 | Van Tassel et al. |
| 2001/0005789 A1 * | 6/2001 | Root et al. .................. 606/200 |
| 2001/0049486 A1 | 12/2001 | Evans et al. |
| 2002/0022860 A1 | 2/2002 | Borillo et al. |
| 2002/0035374 A1 | 3/2002 | Borillo et al. |
| 2003/0023262 A1 | 1/2003 | Welch |
| 2003/0023266 A1 | 1/2003 | Borillo et al. |
| 2003/0057156 A1 | 3/2003 | Peterson et al. |
| 2003/0120337 A1 | 6/2003 | Van Tassel et al. |
| 2003/0181942 A1 | 9/2003 | Sutton et al. |

FOREIGN PATENT DOCUMENTS

| | | |
|---|---|---|
| WO | WO 98/17187 | 4/1998 |
| WO | WO 99/05977 | 2/1999 |
| WO | WO 99/07289 | 2/1999 |
| WO | WO 99/07294 | 2/1999 |
| WO | WO 99/08607 | 2/1999 |
| WO | WO 99/30640 | 6/1999 |
| WO | WO 00/27292 | 5/2000 |
| WO | WO 01/30266 | 5/2001 |
| WO | WO 01/30267 | 5/2001 |
| WO | WO 01/30268 | 5/2001 |
| WO | WO 02/15793 | 2/2002 |
| WO | WO 02/24106 | 3/2002 |
| WO | WO 02/071977 | 9/2002 |

OTHER PUBLICATIONS

Guy S. Reeder, MD et al., "Apiration Thrombectomy for Removal of Coronary Thrombus," The American Journal of Cardiology, p. 107–110, (Jul. 1, 1992).

F. Poulain et al., "Local Thrombolysis and Thromboaspiration in the Treatment of Acutely Thrombosed Arteriovenous Hemodialysis Fistulas," Cardiovascular Intervent Radiology, Spinger–Verlag New York Inc., p. 98–101, (1991).

Hans–Joachim Wagner et al., "Long–Term Results of Percutaneous Aspiration Embolectomy," Cardio Vascular and International Radiology, Springer–Verlag New York Inc., vol. 17, p. 241–246, (1994).

Erhard E. Starck, MD et al., "Percutaneous Aspiration Thromboembolectomy," Radiology, p. 61–66, (Jul., 1985).

Rolf W. Guenther, MD et al., "Aspiration Catheter for Percutaneous Thrombectomy: Clinical Results[1]," Radiology, vol. 175 (No. 1) p. 271–273, (1990).

Melhem J. A. Sharafuddin MD et al., "Percutaneous Balloon–assisted Aspiration Thrombectomy of Clotted Hemodialysis Access Grafts[1]," Journal of Vascular and International Radiology, vol. 7 (No. 1), p. 177–183, (1996).

Luc Turmel–Rodrigues, MD et al., "Manual Thromboaspiration and Dilation of Thombosed Dialysis Access: Midterm Results of a Simple Concept[1]," Journal of Vascular and International Radiology, vol. 8 (No. 5), p. 813–824, (1997).

Tatsuaki Murakami, MD et al., "Intracoronary Aspiration Thrombectomy for Acute Myocardial Infarction," The American Journal of Cardiology, Excerpia Medica, Inc., vol. 82, p. 839–844 (Oct. 1, 1998).

Jacob Shani, MD et al., "Mechanical Manipulation of Thrombus: Coronary Thrombectomy, Intracoronary Clot Displacement, and Transcatheter Aspiration," The American Journal of Cardiology, vol. 72, p. 116G–118G, (Dec. 16, 1993).

Mark Dooris, MBBS et al., "Successful Reversal of Cardiogenic Shock Precipitated by Saphenous Vein Grafft Distal Embolization Using Aspiration Thrombectomy," Catherization and Cardiovascular Diagnosis, Wiley–Liss, Inc., vol. 33, p. 267–271, (1994).

S. Mitchell Rivitz et al., Percutaneous Aspiration Thrombectomy of an Acutely Occluded Aortoernal Bypass Graft, Interventional Radiology Case Conference Massachusetts General Hospital, American Journal of Radiology, p. 455–458, (1995).

Letters to Editor regarding article entitled, "Percutaneous Aspiration Thromboembolectomy", written by Klaus Rauber, MD.

* cited by examiner

CARDIAC STIMULATING APPARATUS HAVING A BLOOD CLOT FILTER AND ATRIAL PACER

CROSS-REFERENCE TO RELATED APPLICATIONS

This Application claims the benefit of U.S. Provisional Application 60/295,683, which was filed on Jun. 4, 2001.

FIELD OF THE INVENTION

The present invention relates generally to a device that deters migration of emboli from an atrial appendage into the vascular system of a patient, and more particularly to a device that includes a filter to deter such migration and a pacer to deter the formation of emboli such as blood clots within the atrial appendage.

BACKGROUND OF THE INVENTION

Non-rheumatic atrial fibrillation (NRAF) is associated with thromboembolic complications such as strokes. For example, when a thrombus or embolus occludes a vessel supplying blood to the brain, a stroke may result causing temporary or lasting paralysis of a part of the body or, in severe cases, death. Blockage of other blood vessels can occur as well causing attendant health concerns, including heart attack or gangrene. Presently, a five percent risk of stroke per year in a largely aging population causes NRAF to be a significant health concern. Given the potentially irreversible and destructive nature of such blood vessel occlusion, safe and effective methods are needed to eliminate embolic material like blood clots from the vascular system, some of which may be formed within an atrial appendage of the heart.

The left atrial appendage forms a small protrusion which is attached to the lateral wall of the left atrium between the mitral valve and the root of the left pulmonary vein and normally contracts along with the left atrium. Atrial fibrillation is a cardiac condition wherein the atria beat faster than the ventricles, causing the ventricles to contract irregularly and consequently eject less blood into the vascular system. A major problem associated with atrial fibrillation is pooling of blood in the left atrial appendage.

During NRAF the left atrial appendage may not fully contract, leaving stagnant blood within the left atrial appendage. In turn, the stagnant blood may create a condition favorable to the formation of blood clots within the left atrial appendage. Such clots may travel from the left atrial appendage into the left atrium and into the vascular system, thereby increasing the danger of stroke or cardiac blockage.

Traditional treatments to mitigate the risks posed by blood clots include the use of anticoagulants to dissolve the clots. For example, recently published results from stroke prevention trials suggest that prophylaxis with anticoagulation is beneficial to patients with non-rheumatic, non-valvular atrial fibrillation. Current therapeutic interventions include anticoagulation with coumedin. In addition, therapeutic interventions include the use of atrial rate regulating medications. However, both of these treatment approaches pose potential complications such as internal bleeding, as well as other negative side effects caused by the rate regulating therapeutic agents.

In addition to pharmacological treatments, complex radical surgical methods are available to treat atrial fibrillation. Such treatments include, for example, atrial incisions or removal of the left atrial appendage, which have been attempted in a limited, experimental way. Such approaches are highly invasive and pose a risk of mortality to the patient. Thus, a pressing need exists for means by which the formation of blood clots the left atrial appendage is substantially deterred while preventing the migration of any blood clots which may form from entering the vascular system.

U.S. Pat. No. 6,152,144 to Lesh et al., for example, discloses a device and method for obliterating or occluding a body cavity or passageway. Specifically, the patent to Lesh is directed to a device and method for obliterating or occluding the left atrial appendage of a patient's heart. In one embodiment, Lesh et al. disclose a frame structure having a barrier or mesh material disposed over it to act as a barrier to the passage of embolic material.

However, Lesh et al. do not disclose a device or method suited to treat atrial fibrillation, or other arrhythmias of the heart, to thereby prevent the formation of clots in the left atrial appendage. As such, the barrier embodiment of Lesh et al. permits ongoing formation of clots within the left atrial appendage, which may eventually occlude the barrier material to prevent fluid flow as well as embolic material flow through the occluded barrier. Such a situation may present a health concern as the left atrial appendage contracts and the blood enclosed therein is unable to exit the left atrial appendage. Such contraction may result in an increased pressure in the left atrial appendage capable of weakening the wall of the left atrial appendage. Additionally, as the barrier embodiment of Lesh et al. does not prevent the formation of clots, it is possible that the volume of the left atrial appendage may eventually be filled with coagulated blood. Thus, filtering alone poses possible added health concerns.

Regarding the treatment of atrial fibrillation, it is known to use a pacemaker, for example, as disclosed in U.S. Pat. No. 6,178,351 B1 to Mower. Mower discloses a pacemaker that is capable of pacing the atria from multiple sites, but does not address prevention of migration of embolic material within the vascular system. Moreover, neither Mower nor Lesh suggests combining a pacer with an embolic barrier for use in the heart.

Accordingly, there is a need for an apparatus for mitigating the risks associated with emboli originating in the left atrial appendage and also for reducing the tendency of such emboli, such as blood clots, to form therein.

SUMMARY OF THE INVENTION

An apparatus is provided for deterring the formation and migration of blood clots from an atrial appendage, such as a left or right atrial appendage, into the blood vessel system, i.e. vascular system, of a patient. In particular, an apparatus of the present invention comprises an atrial pacer to treat non-rheumatic atrial fibrillation (NRAF) or other arrhythmias of an atrial appendage so that the formation of blood clots within such atrial appendage is decreased or eliminated. In addition, the apparatus provides a blood clot filter to deter the migration of blood clots from an atrial appendage into the blood vessel system of a patient.

More specifically, the apparatus comprises a filter for reducing the transport of emboli from an atrial appendage to an atrium of the heart. The filter is formed to provide a structure suitable for separating blood clots from the blood and for reducing passage of blood clots from the atrial appendage into the atrium and general circulation. In accordance with one aspect of the invention, the filter can take the form of a plurality of spokes extending outwardly from the atrial pacer. In another aspect, the filter can take the form of a mesh having pores sized to deter the passage of blood clots.

In accordance with another aspect of the invention, the apparatus comprises an atrial pacer which supports the filter between an atrial appendage and the atrium. The atrial pacer is adapted to be in contact with a wall of the atrial appendage so the atrial pacer may detect and reduce atrial fibrillation in the atrial appendage. The pacer also includes a sensor which may form an integral part of the atrial pacer for sensing fibrillation in the atrial appendage. In an alternative arrangement, the sensor may be adapted to be positioned externally to the heart. In this external arrangement, a lead wire may be provided between the sensor and the atrial wall, to provide sensing contact between the sensor and the atrial wall. The atrial pacer also comprises a stimulator for stimulating the atrial appendage. The simulator may take the form of an electrode for making electrical contact with the wall of the atrial appendage to apply stimulating signals to the atrial appendage. The stimulator may be activated in response to a signal from the sensor indicating the presence of NRAF, or other arrythmias, in the atrial appendage.

A control unit adapted to be positioned externally to the heart may optionally be provided for controlling the atrial pacer. The control unit may communicate with the sensor and/or the stimulator using a lead wire or wireless technology. In addition, the sensor may be disposed within the control unit. For example, in the arrangement where the sensor is positioned externally to the heart, the sensor may be incorporated within the control unit.

BRIEF DESCRIPTION OF THE DRAWINGS

The foregoing summary and the following detailed description of the preferred embodiments of the present invention will be best understood when read in conjunction with the appended drawings, in which.

DETAILED DESCRIPTION OF THE INVENTION

A cardiac stimulating apparatus 10, 100 is provided for substantially reducing the formation of blood clots in an atrial appendage of a heart, such as the left atrial appendage 210, and reducing the migration of such clots into the blood vessel system of a patient. The apparatus 10, 100 comprises a filtration device 28, 124 to reduce migration of embolic material, such as blood clots or the like. In addition, the apparatus 10, 100 includes an atrial pacer 12, 112 to treat arrythmias, such as non-rheumatic atrial fibrillation (NRAF), of the left atrial appendage 210 to deter the formation blood clots within the left atrial appendage 210. FIGS. 1–4 depict the general structure of a cardiac stimulating apparatus of the present invention, illustrating the cooperation between the atrial pacer 12, 112 and the filtration device, such as filter 28 or spokes 124.

Figure 1:
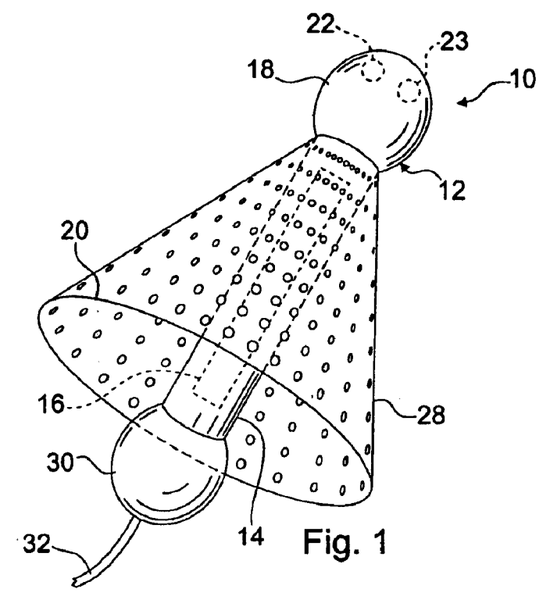
FIG. 1 is a schematic perspective view showing an exemplary device of the present invention having a mesh filter.
Figure 3:
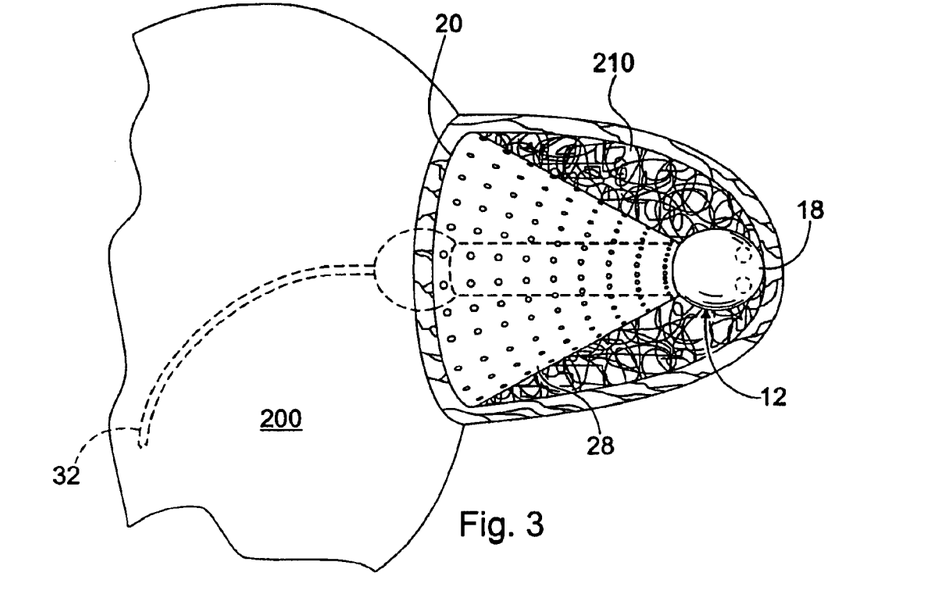
FIG. 3 is a schematic view of the exemplary device shown in FIG. 1 disposed within a left atrial appendage.

Turning now to FIGS. 1 and 3, an embodiment of the present invention is shown in which a cardiac stimulating apparatus 10 comprises an atrial pacer 12 having an elongated generally tubular body 14 having first and second opposing ends 18, 30. The first end 18 of the atrial pacer 12 is adapted to contact the wall of the left atrial appendage 210 to support the cardiac stimulating apparatus 10 within the left atrial appendage 210. The first end 18 may include a sensing device 22 optionally disposed therein to detect NRAF or other arrhythmias in the left atrial appendage 210. In such a configuration, the sensing device 22 is adapted to be in sensing contact with the wall of the left atrial appendage 210. The first end 18 of the atrial pacer 12 also includes a stimulating device 23 for stimulating the left atrial appendage 210 in response to detection of NRAF by a detector, such as sensing device 22. The stimulating device 23 includes an electrode adapted to be in electrical contact with the wall of the atrial appendage 210 for applying stimulating signals to the atrial appendage 210. By application of an appropriate stimulating signal, NRAF can be reduced or eliminated thereby reducing the tendency of blood within the left atrial appendage 210 to form blood clots. The sensing device 22 and stimulating device 23 may comprise components known for use in atrial pacers.

Extending outwardly from the elongated generally tubular body 14, a filtration device is provided to deter the migration of blood clots from the left atrial appendage 210 into the left atrium 200 of the heart. As shown in FIG. 1, an embodiment of the filtration device may take the form of a mesh-like or sieve-like filter 28. The filter 28 may have a generally conical shape as shown, for example, with the narrower end of the conical filter 28 attached to the atrial pacer 12 proximate to the first end 18 of the atrial pacer 12. Alternatively, the filter 28 may be attached to the atrial pacer 12 at any point along the elongated body 14. The filter 28 may have any shape suited to substantially fill the opening defined by the intersection of the left atrial appendage 210 and the left atrium 200, such as a portion of a sphere, flat sheet, or other shape.

Figure 8:
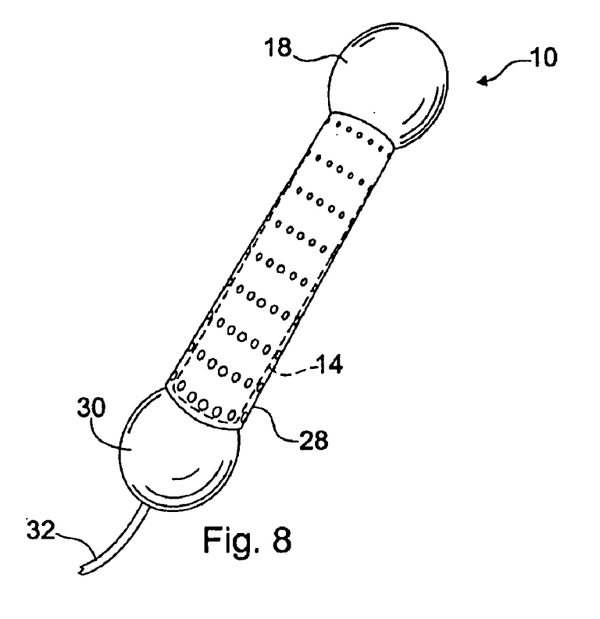
FIG. 8 is a schematic view of the exemplary device shown in FIG. 1 with the filter collapsed against the body of the device.

The mesh-like material of the filter 28 may be formed from a metal, such as a stainless-steel, for example. Alternatively, the filter 28 may be formed from a polymeric material, such as a Nylon or Dacron mesh. Other suitable materials such as PTFE or polyamides may also be used. In particular, it is preferable that the filter 28 be formed of a resilient material capable of being collapsed about the body 14 of the atrial pacer 12, as shown in FIG. 8, to facilitate introduction of the cardiac stimulating device 10 into a patient, for example, via a catheter. The resilient material is chosen such that upon removal of the cardiac stimulating device 10 from the catheter, the filter 28 expands to a desired shape and size to permit the opening of the left atrial appendage 210 to be substantially sealed. Regardless of the material from which the filter 28 is formed, the filter 28 is formed to provide pores having a transverse dimensions of about 1 mm or other size sufficiently small to prevent the passage of blood clots or other thromboembolic material of like or greater size. In particular, it may be desirable for the pore size to have a transverse dimension up to about 0.1 mm.

The wider end of the filter 28 includes a rim portion 20 which defines the is base of the filter 28. The rim portion 20 is sized to circumscribe the opening between the left atrial appendage 210 and left atrium 200, so that emplacement the cardiac stimulating device 10 in the left atrial appendage 210 generally positions the rim portion 20 near the opening left atrial appendage 210 so as to form and maintain a seal therewith. To effect and maintain such a seal, the rim portion 20 may be formed of or covered by a soft polymer material. The rim portion 20 may have a transverse dimension of about 2 to 40 mm, preferably about 25 to 35 mm. The transverse dimension of the rim portion 20 should be selected with regard to the size of the left atrial appendage opening, which may vary among patients, especially those patients having heart disease related conditions.

The rim portion 20 may also include a plurality of holes through which sutures may be placed to anchor the rim portion 20 proximate to the opening of the left atrial appendage 210. Alternatively or additionally, the rim portion 20 may have a spring-like action which causes the rim portion 20 to expand generally radially outward from the longitudinal axis of the atrial pacer 12, so that the rim portion 20 applies pressure against a region proximate the opening of the left atrial appendage 210 to form a seal proximate the opening of the left atrial appendage 210. For example, the rim portion 20 may be formed of a shape memory metal, such as NiTi, having a memorized shape larger than that of the opening of the left atrial appendage 210 to supply the radially outward pressure on the opening. The filter 28 is attached to the atrial pacer 12 at such a location so as to permit the rim portion 20 to substantially form a seal within the left atrial appendage opening and to permit the first end 18 of the atrial pacer 12 to contact the wall of the atrial appendage 210.

Figure 2:
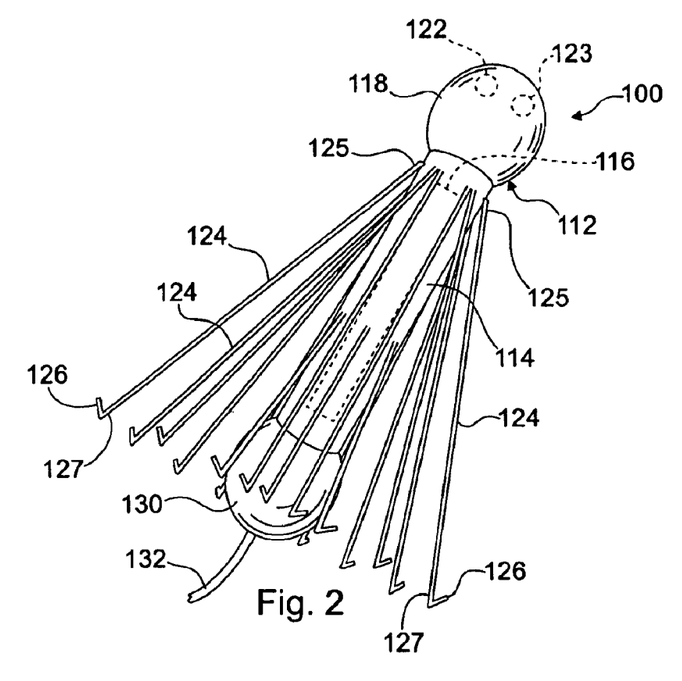
FIG. 2 is a schematic perspective view showing an exemplary device of the present invention having a filter which includes a plurality of spokes.
Figure 4:
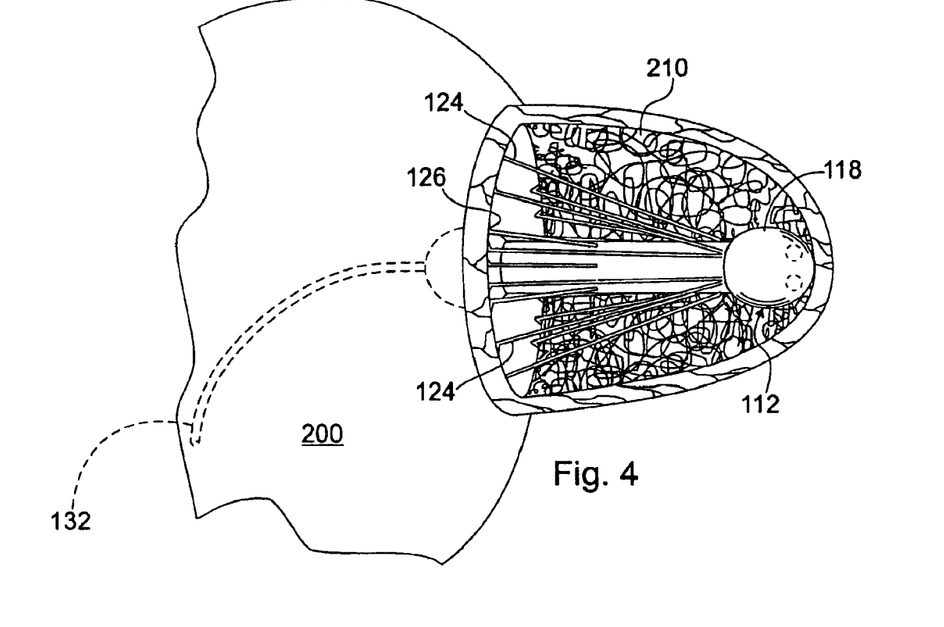
FIG. 4 is a schematic view of the exemplary device shown in FIG. 2 disposed within a left atrial appendage.

Referring now to FIGS. 2 and 4, an alternative embodiment of the cardiac stimulating apparatus 100 is shown where the filtration device comprises a plurality of spokes 124 extending generally radially outwardly from the atrial pacer 112, to deter the migration of blood clots from the left atrial appendage 210 of the heart to the left atrium 200 of the heart. The atrial pacer 112 of the alternative embodiment comprises an elongated generally tubular body 114 having first and second ends 118, 130, a stimulating device 123, and an optional sensing device 122 similar to like components 23 and 22 described above with regard to the previous embodiment.

The spokes 124 each comprise a first end 125 attached to the elongated body 114 of the atrial pacer 112 and a second end 127 of the spokes 124 for engaging a region of the heart in the vicinity of the left atrial appendage 210. The second end 127 of the spokes 124 may terminate in a hook-like tine 126 formed to anchor the spokes 124 and retain the atrial pacer 112 within the left atrial appendage 210. In addition, all or some of the second ends 127 of the spokes 124 may include a hole suitable for placing a suture therethrough for attachment to the left atrial appendage 210. The number of spokes 124 employed should be sufficiently numerous to create interstices between the spokes 124 sufficiently small to deter the passage of embolic material through the interstices.

The first ends 125 of the plurality a spokes 124 may be attached to the body 114 of the atrial pacer 112 at a common distance from the first end 118 of the atrial pacer 112. Alternatively, the first ends 125 of the plurality of spokes 124 may be attached to the body 114 of the atrial pacer 112 at varying distances from the first end 118 of the atrial pacer 112. Providing spokes 124 at a variety of distances from the first end 118 of the atrial pacer 112 may be useful to create a tortuous path to deter the flow of embolic material. For example, a first set of spokes 124 may have first ends 125 adjoining the atrial pacer 112 at a common distance from the first end 118 around the circumference of the atrial pacer 112. A second set of spokes may have first ends adjoining the atrial pacer 112 at a further distance from the first end 118 of the atrial pacer 112 than the first set of spokes 124. In addition, the second set of spokes may be oriented circumferentially to overlap with the interstices formed among the first set of spokes 124, as viewed from the first end 118 of the atrial pacer 112. Likewise, additional set of spokes 124 may be included to effect additional blockage of embolic material flow. Moreover, some or all of the spokes 124 may extend outwardly from the atrial pacer 112 along non-radial directions, to enhance blockage of embolic material.

Figure 9:
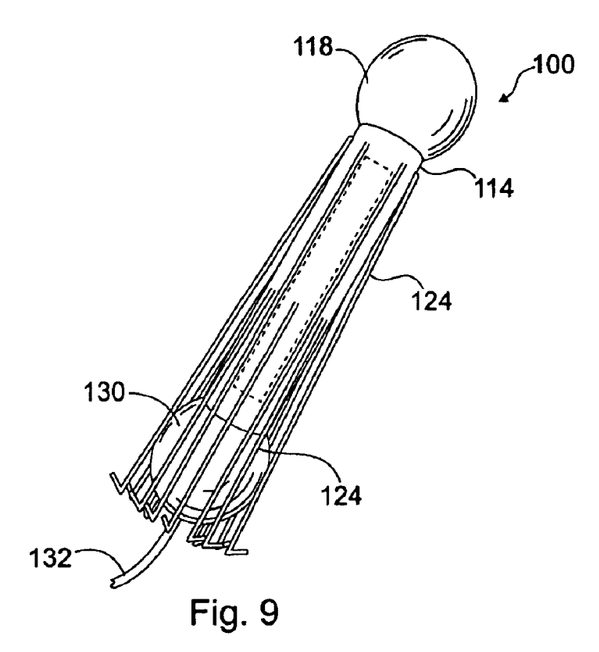
FIG. 9 is a schematic view of the exemplary device shown in FIG. 2 with the spokes collapsed against the body of the device.

The spokes 124 may be formed of any suitable material such as a metal or polymeric material like those described above with regard to the mesh-like filter 28. It is also desirable that the spokes 124 be sufficiently pliable to permit the spokes 124 to be disposed along the body 114 of the atrial pacer 112, as shown in FIG. 9, while the cardiac stimulating device 100 is placed into a patient via a catheter.

In addition, it is desirable that the spokes 124 be sufficiently resilient so that they expand away from the body 114 of the atrial pacer 112 once removed from the catheter, permitting the spokes 124 to engage the wall of left atrial appendage 210. In addition, the spokes 124 are formed sufficiently long and disposed at an angle away from the body 114 of the atrial pacer 112 to cause the second ends 127 of the spokes 124 to be biased against the wall of the left atrial appendage 210 to retain the cardiac stimulating device 100 in position. For example, the spokes 125 may have a length to allow the second ends 127 of the spokes 124 to terminate proximate the left atrial appendage opening. The spokes 124 are attached to the atrial pacer 112 at such a location as to permit the spokes 124 to partially occlude the opening of the left atrial appendage and to permit the first end 118 of the atrial pacer 112 to contact the wall of the atrial appendage 210.

In each of the above embodiments, the atrial pacer 12, 112 may include a power source 16, 116, such as a rechargeable battery, within the generally elongated body 14, 114 along with appropriate circuitry known for the operation of atrial sensing and stimulating devices. Alternatively or additionally, the cardiac stimulating device 10, 100 may include a lead wire 32, 132 to provide power and/or a control signal to the atrial pacer 12, 112 from a remote device. A control unit for use external to the left atrial appendage 210, or external to a patient's body, may be provided for housing circuitry of the atrial pacer 12, 112. Providing such a control unit may also be desirable, since inclusion of control circuitry therein may permit the atrial pacer 12, 112 to have a smaller overall the size.

Figure 5:
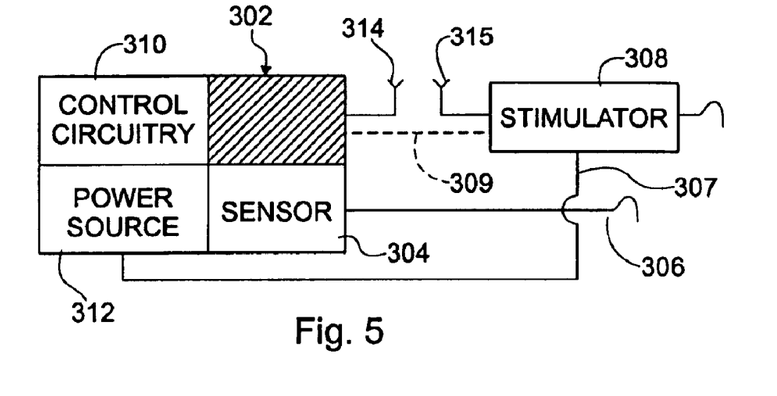
FIG. 5 is a schematic block diagram of a first exemplary configuration of an atrial pacer of the present invention having a control unit which includes a sensor and lead wire for detecting a selected condition of the heart.
Figure 6:
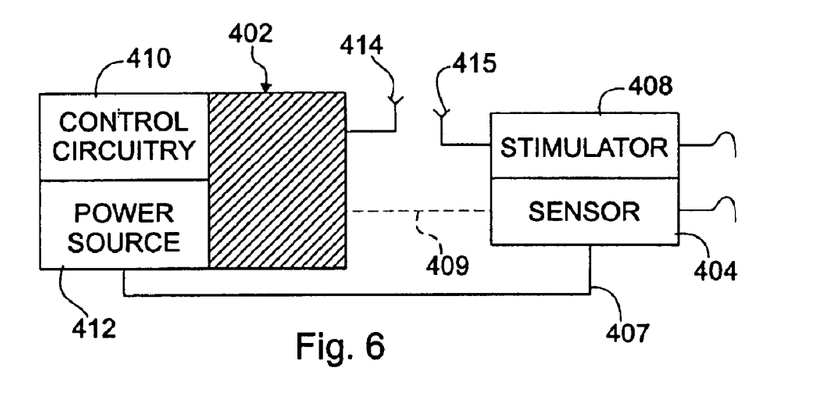
FIG. 6 is a block diagram of a second exemplary configuration of an atrial pacer of the present invention having a control unit for communication with stimulator and sensor.
Figure 7:
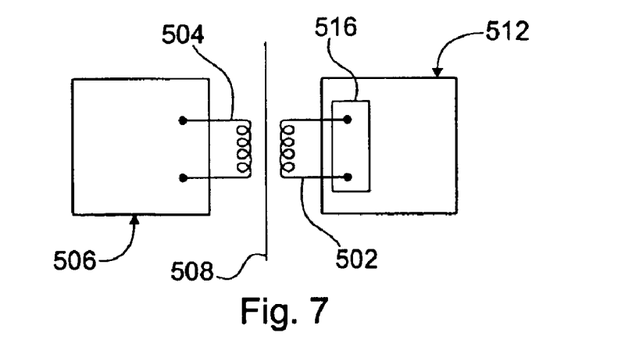
FIG. 7 is a block diagram of a rechargeable configuration of an atrial pacer of the present invention.

Referring to FIGS. 5–7, three exemplary embodiments are shown of device arrangements which include remote control and/or power supply units. In particular, with regard to FIG. 5, a control unit 302 is shown for controlling and powering the stimulator 308 of an atrial pacer. The stimulator 308 may correspond to the stimulating devices 23, 123 depicted in FIGS. 1 and 2 as described above. In the configuration of FIG. 5, a sensor 304 is incorporated in a remotely located control unit 302 rather than in the elongated body 14, 114 of the atrial pacer 12, 112. The sensor 304 is in sensing contact with the left atrial appendage 210 via lead wire 306 to detect NRAF in the atrial appendage 210. Hence, for this configuration the sensing device 22, 122 described above as being disposed within the first end 18, 118 of the atrial pacer 12,112 is not required to be disposed therein.

The control unit 302 further includes control circuitry 310 for processing the signal detected by the sensor 304 and controlling the stimulator 308 in response to the detected signal. For example, when the control circuitry 310 receives a signal from the sensor 304 indicative of NRAF of the left atrial appendage 210, the control circuitry delivers a control signal to the stimulator 308 to cause the stimulator 308 to stimulate the left atrial appendage 210 to alleviate the NRAF. Hence, by correcting NRAF, formation of blood clots in the left atrial appendage 210 is reduced by limiting the presence of stagnant blood in the left atrial appendage 210. The control unit 302 communicates with the stimulator 308 via an optional lead wire 309 or via wireless communication.

Wireless communication can be effected via optional antennas 314, 315 connected to the control unit 302 and the stimulator 308, respectively. The antenna 315 of the stimulator 308 may be disposed, for example, at the second end 30, 130 of the atrial pacer 12, 112. The control unit 302 may include a power source 312 to power the control unit 302 and to optionally power the stimulator 308 via lead wire 307.

Referring to FIG. 6, a further embodiment of the present invention is shown which is substantially similar to that shown in FIG. 5. The embodiment of FIG. 6 differs from FIG. 5 in that the control unit 402 of FIG. 6 does not include a sensor. Instead, a sensor 404 is provided in the elongated body 14, 114 of the atrial pacer 12, 112 along with a stimulator 408. Such a sensor 404 may correspond to the sensing devices 22, 122 shown in FIGS. 1 and 2 and described above. Since the sensor 404 and stimulator 408 are both disposed within the body 14, 114 of the atrial pacer 12, 112, the sensor 404 and stimulator 408 may communicate directly with each other so that the stimulator 408 may stimulate left atrial appendage 210 in response to the detection of NRAF by the sensor 404. Alternatively, to minimize the size of the atrial pacer, control circuitry may be provided in a remote control unit 402 to receive data from the sensor 404, to process such data, and control the stimulator 408 in response to such data. Communication between the control unit 402 and the stimulator 408 and sensor 404 may be effected via an optional lead wire 409 or via wireless communication using optional antennas 414, 415, in a similar manner to that described above with regard to the embodiment of FIG. 5.

In addition, as shown in FIG. 7, the atrial pacer 512 may be configured to be recharged by a remote charger 506. In such an embodiment, the atrial pacer 512 includes a first electrical coil 502 electrically coupled to an energizer unit 516, such as a battery, of the atrial pacer 512. The recharger 506 has a corresponding second electrical coil 504 which may be electromagnetically coupled to the first coil 502 to transmit electromagnetic energy thereto from the charger 506, through the patient's skin 508, and thence into the energizer unit 516 of the atrial pacer 512.

After insertion of the cardiac stimulating device 10, 100 into the heart so that the filtration device 28, 126 expands and sensing device 22, 122 or sensor 304, 404 is placed in sensing contact with the left atrial appendage 210, the cardiac stimulating device 10, 100 monitors for the presence of NRAF. Upon detection of NRAF, the stimulator 23, 123 applies a correcting stimulating electrical signal to the left atrial appendage 210 in response to the detected NRAF condition. By such treatment of the left atrial appendage 210 to minimize NRAF, the formation of blood clots attributable to NRAF is minimized. In addition, the presence of the filtration device 28, 126 provides continuous filtration of the blood exiting the left atrial appendage 210, so as to prevent the egress of emboli therefrom.

These and other advantages of the present invention will be apparent to those skilled in the art. Accordingly, it will be recognized by those skilled in the art that changes or modifications may be made to the above-described embodiments without departing from the broad inventive concepts of the invention. For example, the atrial pacer could be replaced and/or adapted to function as a ventricular defibrillator to treat ventricular tachycardia. Likewise, the atrial pacer could be replaced by a device that functions as a combined atrial pacer and ventricular defibrillator. It should therefore be understood that this invention is not limited to the particular embodiments described herein, but is intended to include all changes and modifications that are within the scope and spirit of the invention as set forth in the claims.

What is claimed is:

1. A cardiac stimulating apparatus, comprising:
   a filter adapted to substantially prevent transport of emboli from an atrial
   appendage to an atrium of the heart; and
   an atrial pacer to support the filter between the atrial appendage and the atrium, the atrial pacer adapted to be in sensing contact with a wall of the atrial appendage to reduce atrial fibrillation in the atrial appendage.

2. The cardiac stimulating apparatus according to claim 1 wherein the filter comprises a plurality of spokes.

3. The cardiac stimulating apparatus according to claim 2 wherein the spokes include tines to attach the filter to the atrial appendage.

4. The cardiac stimulating apparatus according to claim 1 wherein the spokes extend generally radially outwardly from the atrial pacer.

5. The cardiac stimulating apparatus according to claim 1 wherein the filter comprises a mesh.

6. The cardiac stimulating apparatus according to claim 1 wherein the filter includes at least one of an expandable mesh and a plurality of expandable spokes.

7. The cardiac stimulating apparatus according to claim 6 wherein said one of said expendable mesh and said plurality of expendable spokes are collapsible to be disposed near the atrial pacer for implantation into the atrial appendage through a catheter.

8. The cardiac stimulating apparatus according to claim 1 wherein atrial pacer includes a control unit adapted to be disposed external to the heart.

9. The cardiac stimulating apparatus according to claim 8 wherein, the control unit includes a sensor adapted to be in sensing contact with the wall of the atrial appendage.

10. The cardiac stimulating apparatus according to claim 9 wherein the control unit is adapted to be in wireless communication with the sensor.

11. The cardiac stimulating apparatus according to claim 8 wherein the control unit comprises circuitry for providing a control signal to control the atrial pacer.

12. The cardiac stimulating apparatus according to claim 8 wherein the atrial pacer includes a stimulator adapted to be disposed interior to the heart for applying a stimulating signal to the wall of the atrial appendage.

13. The cardiac stimulating apparatus according to claim 12 wherein the control unit is adapted to be in wireless communication with the stimulator.

14. The cardiac stimulating apparatus according to claim 12 wherein the control unit is adapted to be in wireless communication with the electrode.

15. The cardiac stimulating apparatus according to claim 1 wherein the atrial pacer includes at least one of a stimulator disposed therein for applying a stimulating signal to the wall of the atrial appendage and a sensor disposed therein to be in sensing contact with a wall of the atrial appendage.

16. The cardiac stimulating apparatus according to claim 1 comprising:
  i) a charger adapted to be disposed external to a patient's body for providing a power signal in the form of electromagnetic energy; and
  ii) an energizer adapted to be disposed internal to a patient's body for receiving the power signal provided by the generator unit to energize said atrial pacer.

17. The cardiac stimulating apparatus according to claim 16 wherein the charger and the energizer are in wireless communication.

18. The cardiac stimulating apparatus according to claim 16 wherein the generator unit comprises a first coil for transmitting the power signal and the energizing unit comprises a second coil for receiving the power signal.

19. A cardiac stimulating apparatus, comprising:
  a filter adapted to engage proximate an opening between an atrial appendage and an atrium of a heart; and
  an atrial pacer to support the filter proximate the opening between the atrial appendage and the atrium, comprising
    i) a sensor adapted to be in sensing contact with a wall of the atrial appendage for sensing fibrillation of the atrial appendage, and
    ii) an electrode adapted to be in electrical contact with the wall of the atrial appendage for applying stimulating signals to the atrial appendage.

20. The cardiac stimulating apparatus according to claim 19 wherein the filter comprises a plurality of spokes.

21. The cardiac stimulating apparatus according to claim 20 wherein the spokes include tines to attach the filter to the atrial appendage.

22. The cardiac stimulating apparatus according to claim 19 wherein the spokes extend generally radially outwardly from the atrial pacer.

23. The cardiac stimulating apparatus according to claim 19 wherein the filter comprises a mesh.

24. The cardiac stimulating apparatus according to claim 19 wherein the filter includes at least one of an expandable mesh and a plurality of expandable spokes.

25. The cardiac stimulating apparatus according to claim 24 wherein said one of said expendable mesh and said plurality of expendable spokes are collapsible to be disposed near the atrial pacer for implantation into the atrial appendage through a catheter.

26. The cardiac stimulating apparatus according to claim 19 wherein atrial pacer includes a control unit adapted to be disposed external to the heart.

27. The cardiac stimulating apparatus according to claim 26 wherein the control unit is adapted to be in wireless communication with the sensor.

28. The cardiac stimulating apparatus according to claim 26 wherein the control unit comprises circuitry for providing a control signal to control the atrial pacer.

29. The cardiac stimulating apparatus according to claim 19 wherein the atrial pacer includes a stimulator for providing a stimulation control signal to the electrode.

30. The cardiac stimulating apparatus according to claim 19 comprising:
  i) a charger adapted to be disposed external to a patient's body for providing a power signal in the form of electromagnetic energy; and
  ii) an energizer adapted to be disposed internal to a patient's body for receiving the power signal provided by the generator unit to energize said atrial pacer.

31. The cardiac stimulating apparatus according to claim 30 wherein the generator unit comprises a first coil for transmitting the power signal and the energizing unit comprises a second coil for receiving the power signal.

32. A cardiac stimulating apparatus, comprising:
  a filtration device for reducing the transport of emboli from an atrial appendage to an atrium of the heart; and
  an atrial pacer to support the filtration device between the atrial appendage and the atrium, the atrial pacer adapted to contact a wall of the atrial appendage for reducing atrial fibrillation in the atrial appendage.

33. The cardiac stimulating apparatus according to claim 32 wherein the filtration device comprises a plurality of spokes.

34. The cardiac stimulating apparatus according to claim 33 wherein the spokes include tines to attach the filtration device to the atrial appendage.

35. The cardiac stimulating apparatus according to claim 32 wherein the spokes extend generally radially outwardly from the atrial pacer.

36. The cardiac stimulating apparatus according to claim 32 wherein the filtration device comprises a mesh.

37. The cardiac stimulating apparatus according to claim 32 wherein the filtration device includes at least one of an expandable mesh and a plurality of expandable spokes.

38. The cardiac stimulating apparatus according to claim 37 wherein said one of said expendable mesh and said plurality of expendable spokes are collapsible to be disposed near the atrial pacer for implantation into the atrial appendage through a catheter.

39. The cardiac stimulating apparatus according to claim 32 wherein atrial pacer includes a control unit adapted to be disposed external to the heart.

40. The cardiac stimulating apparatus according to claim 39 wherein, the control unit includes a sensor adapted to be in sensing contact with the wall of the atrial appendage.

41. The cardiac stimulating apparatus according to claim 40 wherein the control unit is adapted to be in wireless communication with the sensor.

42. The cardiac stimulating apparatus according to claim 39 wherein the control unit comprises circuitry for providing a control signal to control the atrial pacer.

43. The cardiac stimulating apparatus according to claim 39 wherein the atrial pacer includes a stimulator adapted to be disposed interior to the heart for applying a stimulating signal to the wall of the atrial appendage.

44. The cardiac stimulating apparatus according to claim 43 wherein the control unit is adapted to be in wireless communication with the stimulator.

45. The cardiac stimulating apparatus according to claim 32 wherein the atrial pacer includes at least one of a stimulator disposed therein for applying a stimulating signal to the wall of the atrial appendage and a sensor disposed therein to be in sensing contact with a wall of the atrial appendage.

46. The cardiac stimulating apparatus according to claim 32 comprising:
  i) a charger adapted to be disposed external to a patient's body for providing a power signal in the form of electromagnetic energy; and ii) an energizer adapted to be disposed internal to a patient's body for receiving the power signal provided by the generator unit to energize said atrial pacer.

47. The cardiac stimulating apparatus according to claim 46 wherein the generator unit comprises a first coil for transmitting the power signal and the energizing unit comprises a second coil for receiving the power signal.

48. A cardiac stimulating apparatus comprising:
an atrial pacer comprising an elongated body adapted at one end thereof for making at least one of sensing and stimulating contact with a wall of an atrial appendage of a heart, said atrial pacer including at least one of an atrial sensor and an atrial stimulator; and
an filtration device mounted to said elongated body distal the one end thereof and adapted for intercepting emboli moving between the atrial appendage and an atrium of the heart.

49. The cardiac stimulating apparatus according to claim 48 wherein the filtration device comprises a plurality of spokes.

50. The cardiac stimulating apparatus according to claim 49 wherein the spokes include tines to attach the filtration device to the atrial appendage.

51. The cardiac stimulating apparatus according to claim 48 wherein the spokes extend generally radially outwardly from the atrial pacer.

52. The cardiac stimulating apparatus according to claim 48 wherein the filtration device comprises a mesh.

53. The cardiac stimulating apparatus according to claim 48 wherein the filtration device includes at least one of an expandable mesh and a plurality of expandable spokes.

54. The cardiac stimulating apparatus according to claim 53 wherein said one of said expendable mesh and said plurality of expendable spokes are collapsible to be disposed near the atrial pacer for implantation into the atrial appendage through a catheter.

55. The cardiac stimulating apparatus according to claim 48 wherein atrial pacer includes a control unit adapted to be disposed external to the heart.

56. The cardiac stimulating apparatus according to claim 55 wherein the control unit is adapted to be in wireless communication with the atrial sensor.

57. The cardiac stimulating apparatus according to claim 55 wherein the control unit is adapted to be in wireless communication with the stimulator.

58. The cardiac stimulating apparatus according to claim 48 wherein the stimulator is adapted to apply a stimulating signal to the wall of the atrial appendage and the sensor is adapted to be in sensing contact with a wall of the atrial appendage.

59. The cardiac stimulating apparatus according to claim 48 comprising:
i) a charger adapted to be disposed external to a patient's body for providing a power signal in the form of electromagnetic energy; and
ii) an energizer adapted to be disposed internal to a patient's body for receiving the power signal provided by the generator unit to energize said atrial pacer.

60. The cardiac stimulating apparatus according to claim 59 wherein the generator unit comprises a first coil for transmitting the power signal and the energizing unit comprises a second coil for receiving the power signal.

61. A cardiac stimulating apparatus comprising:
an atrial pacer comprising an elongated body adapted at one end thereof for making at least one of sensing and stimulating contact with a wall of an atrial appendage of a heart, said atrial pacer including an atrial sensor and an atrial stimulator disposed in said elongated body; and
an filtration device mounted to said elongated body distal the one end thereof and adapted for intercepting emboli moving between the atrial appendage and an atrium of the heart.

62. The cardiac stimulating apparatus according to claim 61 wherein the filtration device comprises a plurality of spokes.

63. The cardiac stimulating apparatus according to claim 62 wherein the spokes include tines to attach the filtration device to the atrial appendage.

64. The cardiac stimulating apparatus according to claim 61 wherein the spokes extend generally radially outwardly from the atrial pacer.

65. The cardiac stimulating apparatus according to claim 61 wherein the filtration device comprises a mesh.

66. The cardiac stimulating apparatus according to claim 61 wherein the filtration device includes at least one of an expandable mesh and a plurality of expandable spokes.

67. The cardiac stimulating apparatus according to claim 66 wherein said one of said expendable mesh and said plurality of expendable spokes are collapsible to be disposed near the atrial pacer for implantation into the atrial appendage through a catheter.

68. The cardiac stimulating apparatus according to claim 61 wherein the atrial pacer includes a control unit adapted to be disposed external to the heart.

69. The cardiac stimulating apparatus according to claim 68 wherein the control unit is adapted to be in wireless communication with the sensor.

70. The cardiac stimulating apparatus according to claim 68 wherein the control unit is adapted to be in wireless communication with the stimulator.

71. The cardiac stimulating apparatus according to claim 61 wherein the stimulator is adapted to apply a stimulating signal to the wall of the atrial appendage and the sensor is adapted to be in sensing contact with a wall of the atrial appendage.

72. The cardiac stimulating apparatus according to claim 61 comprising:
i) a charger adapted to be disposed external to a patient's body for providing a power signal in the form of electromagnetic energy; and
ii) an energizer adapted to be disposed internal to a patient's body for receiving the power signal provided by the generator unit to energize said atrial pacer.

73. The cardiac stimulating apparatus according to claim 72 wherein the generator unit comprises a first coil for transmitting the power signal and the energizing unit comprises a second coil for receiving the power signal.

74. A cardiac stimulating apparatus, comprising:
a filtration means for reducing the transport of emboli from an atrial appendage to an atrium of the heart; and
a pacing means for supporting the filtration device between the atrial appendage and the atrium and for reducing atrial fibrillation in the atrial appendage.

75. The cardiac stimulating apparatus according to claim 74 wherein the filtration means comprises a plurality of spokes.

76. The cardiac stimulating apparatus according to claim 74 wherein the spokes extend generally radially outwardly from the pacing means.

77. The cardiac stimulating apparatus according to claim 74 wherein the filtration means comprises a mesh.

78. The cardiac stimulating apparatus according to claim 74 wherein the filtration means includes at least one of an expandable mesh and a plurality of expandable spokes.

79. The cardiac stimulating apparatus according to claim 78 wherein said one of said expendable mesh and said plurality of expendable spokes are collapsible to be disposed near the pacing means for implantation into the atrial appendage through a catheter.

80. The cardiac stimulating apparatus according to claim 74 wherein pacing means includes a control unit adapted to be disposed external to the heart.

81. The cardiac stimulating apparatus according to claim 80 wherein, the control unit includes a sensor adapted to be in sensing contact with the wall of the atrial appendage.

82. The cardiac stimulating apparatus according to claim 81 wherein the control unit is adapted to be in wireless communication with the sensor.

83. The cardiac stimulating apparatus according to claim 80 wherein the pacing means includes a stimulator adapted to be disposed interior to the heart for applying a stimulating signal to the wall of the atrial appendage.

84. The cardiac stimulating apparatus according to claim 83 wherein the control unit is adapted to be in wireless communication with the stimulator.

85. The cardiac stimulating apparatus according to claim 74 wherein the pacing means includes at least one of a stimulator disposed therein for applying a stimulating signal to the wall of the atrial appendage and a sensor disposed therein to be in sensing contact with a wall of the atrial appendage.

86. The cardiac stimulating apparatus according to claim 74 comprising:
   i) a charger adapted to be disposed external to a patient's body for providing a power signal in the form of electromagnetic energy; and
   ii) an energizer adapted to be disposed internal to a patient's body for receiving the power signal provided by the generator unit to energize said pacing means.

87. The cardiac stimulating apparatus according to claim 86 wherein the generator unit comprises a first coil for transmitting the power signal and the energizing unit comprises a second coil for receiving the power signal.

* * * * *